(12) United States Patent
Sharma et al.

(10) Patent No.: US 12,083,035 B2
(45) Date of Patent: Sep. 10, 2024

(54) FECAL DISCHARGE COLLECTION DEVICE

(71) Applicant: CM Technologies, Inc., San Diego, CA (US)

(72) Inventors: Amit Kumar Sharma, New Delhi (IN); Nishith Chasmawala, Surat (IN); John Everett Martin, Gainesville, FL (US); Abhinav Ramani, Herndon, VA (US); Paul Thomas Hichwa, Mountain View, CA (US)

(73) Assignee: CM Technologies, Inc., San Diego, CA (US)

( * ) Notice: Subject to any disclaimer, the term of this patent is extended or adjusted under 35 U.S.C. 154(b) by 99 days.

(21) Appl. No.: 17/425,075

(22) PCT Filed: Jan. 22, 2020

(86) PCT No.: PCT/IB2020/050490
§ 371 (c)(1),
(2) Date: Jul. 22, 2021

(87) PCT Pub. No.: WO2020/152598
PCT Pub. Date: Jul. 30, 2020

(65) Prior Publication Data
US 2022/0096264 A1  Mar. 31, 2022

Related U.S. Application Data

(60) Provisional application No. 62/795,034, filed on Jan. 22, 2019.

(51) Int. Cl.
*A61F 5/451* (2006.01)
*A61F 5/44* (2006.01)

(52) U.S. Cl.
CPC .......... *A61F 5/451* (2013.01); *A61F 5/4407* (2013.01)

(58) Field of Classification Search
CPC ........ A61F 5/44; A61F 5/451; A61F 9/00781; A61M 27/002
See application file for complete search history.

(56) References Cited

U.S. PATENT DOCUMENTS

| | | | | |
|---|---|---|---|---|
| 4,496,356 A | * | 1/1985 | Lognion | A61F 5/451 604/328 |
| 5,741,239 A | * | 4/1998 | Mulholland | A61F 5/451 604/355 |

(Continued)

OTHER PUBLICATIONS

MatWeb "Overview of materials for Stainless Steel https://matweb.com/search/DataSheet.aspx?MatGUID=71396e57ff5940b791ece120e4d563e0&ckck=1".*

(Continued)

*Primary Examiner* — Philip R Wiest
*Assistant Examiner* — Matthew Wrubleski
(74) *Attorney, Agent, or Firm* — Budzyn IP Law, LLC

(57) ABSTRACT

The present invention provides devices for collection of stool or fecal discharge. In an embodiment said device comprising a retaining component configured for deployment within a subject's rectum and having an annular cross-section, said annular cross-section of the retaining component forming a fluid inlet into an open end of a collection component affixed to said retaining component and forming a receptacle for matter discharged from a subject's rectum.

7 Claims, 9 Drawing Sheets

(56) References Cited

U.S. PATENT DOCUMENTS

| | | | | |
|---|---|---|---|---|
| 2009/0216206 A1* | 8/2009 | Nishtala | ................ | A61F 5/4405 604/327 |
| 2010/0222754 A1* | 9/2010 | Nishtala | ................ | A61F 5/4408 604/328 |
| 2012/0116336 A1* | 5/2012 | Sharma | ................ | A61M 25/04 604/328 |
| 2017/0000642 A1 | 1/2017 | Cisko et al. | | |

OTHER PUBLICATIONS

"Matweb "Overview of materials for Silicone Rubber" https://www.matweb.com/search/DataSheet.aspx?MatGUID=cbe7a469897a47eda563816c86a73520&ckck=1".*

"Stack Exchange Chemistry 'Elasticity of Latex' Nov. 26, 2014 https://chemistry.stackexchange.com/questions/20008/elasticity-of-latex" (Year: 2014).*

"Spring Engineers 'AISI 1095 Spring Steel' Jun. 17, 2017 https://www.springhouston.com/materials/carbon-steel/aisi-1095-spring.html", hereafter StackExchange and Spring Engineers, respectively. (Year: 2017).*

Huyett 'Materials & Attributes' https://www.huyett.com/resources/production-and-design/materials-and-attributes.*

"ISM 'What is Durometer' https://www.industrialspec.com/about-US/blog/detail/what-is-durometer-elastomer-and-plastic-hardness".*

International Search Report from PCT International Application No. PCT/IB2020/050490, dated May 12, 2020.

* cited by examiner

FECAL DISCHARGE COLLECTION DEVICE

CROSS-REFERENCE TO RELATED APPLICATIONS

This Application is a National Stage Application under 35 U.S.C. § 371 of PCT Application No. PCT/IB2020/050490, filed Jan. 22, 2020, which claims priority from and the benefit of U.S. Provisional Patent Application No. 62/795,034 filed Jan. 22, 2019, which are hereby incorporated by reference in their respective entireties.

FIELD OF THE INVENTION

The invention relates to the domain of stool collection, and provides devices for collection of stool or fecal discharge.

BACKGROUND

As contents move through the gastro-intestinal (GI) tract, they pass through the stomach, small intestines, and colon. Stomach acids break down these contents so nutrients can be easily absorbed by the small intestines before reaching the colon where predominantly water is absorbed and stool becomes formed. The rectum is the most distal region of the colon and serves as temporary storage for intestinal effluents before they are expelled. As rectal pressure increases and the rectal wall expands due to materials filling it from within, a desire to defecate occurs. This desire causes the internal anal sphincter muscle to relax and the external sphincter to contract. As rectal peristalsis continues to push effluents towards the anal canal, continued relaxation of the sphincter muscles allow feces to pass. If defecation is not attended to, stool stays in the rectum where water continues to be absorbed and the stool continues to harden. If stool is left in the rectum for long enough, it can cause pain and result in difficulty to expel or pass the stool mass. This is normally called constipation.

When constipation occurs, there are multiple treatments available to help soften the stool and increase the ease of expulsion. These include the use of oral stool softeners and laxatives, as well as suppositories and enemas. Enemas have been established as a quick and effective management technique to aid in the evacuation of colonic contents by administering irrigation liquids via the anus to the intestines, preferably to both the rectum and colon. This helps soften the hardened stool mass, lubricate the rectal tissue, and stimulate contraction of the rectal muscles, called peristalsis. People who become constipated due to disruption of the nervous system or diseases of the colon and rectum often benefit from these procedures. Those who suffer from slow colonic transit, often resulting from immobility or certain medications (such as opioids), benefit from the use of these treatments as well.

Instillation of fluids into the colon is also a common practice for reasons other than stool evacuation. Patients may receive medicated enemas for treatment of certain diseases such as inflammatory bowel disease or infections such as *Clostridium difficile*. Furthermore, fecal microbiota transplants, which involve the administration of healthy liquefied fecal matter into the colon, are becoming more common treatments for the same conditions.

Due to various factors such as traumas, diseases, age, or recent surgery, there are a number of people who are in need of these types of procedures, but are not able to move to a toilet for evacuation. For these groups of bedridden patients, enemas are normally performed while lying down on the bed and effluents are caught with diapers, pads, or bedpans. This causes stool to be exposed to the patient, care provider, and care environment, which is unhygienic and can increase the risk of infections and other complications. Furthermore, the cleaning of these patients and changing of diapers, clothing, and linens quickly becomes time consuming and an economic burden.

Current standards for containment of fecal output in bedridden patients are quickly shifting to the use of indwelling drainage catheters placed in the rectum. Though these have proven efficacious, they have significant limitations in use cases, are known to cause secondary complications, and have been described as uncomfortable or painful by patients. Their limitations and complications include:

Rectum must be clear of any stool before placement.
Must be inserted manually using a finger to place the device.
Collection of liquid to semi-liquid stool only.
Risk of lumen occlusion and/or expulsion if patient has semi-formed to formed stool.
Risk of spontaneous expulsion if patient has weak or damaged anal sphincter muscles.
High pressures placed on tissues causes painful internal ulcers and necrosis.

There is accordingly a need for a fluid delivery and collection device for fecal discharge that addresses the above shortcomings.

SUMMARY

The present invention provides devices for collection of stool or fecal discharge.

An embodiment of the invention comprises a device for collection of fecal discharge, said device comprising a retaining component configured for deployment within a subject's rectum and having an annular cross-section, said annular cross-section of the retaining component forming a fluid inlet into an open end of a collection component affixed to said retaining component and forming a receptacle for matter discharged from a subject's rectum.

The retaining component may include an annular body comprising a first material and a resilient ring comprising a second material, wherein the annular body overlays the resilient ring and forms an outer periphery of the annular retaining component.

The resilient ring may be configured to exert outward radial pressure of between 5 mmHg and 100 mmHg.

The thickness of the first material of the annular body between the resilient ring and an outer circumferential periphery of the retaining component may lie between 1 mm and 20 mm.

The first material and the second material may have either or both of different flexural modulus and different durometer.

In an embodiment of the invention, a first flexural modulus of the first material may be lower than a second flexural modulus of the second material.

In another embodiment, a first durometer of the first material may be lower than a second durometer of the second material.

The first flexural modulus of the first material may lie between 100 KPa and 100 MPa, and the second flexural modulus of the second material may lie between 20 GPa and 210 GPa.

In an embodiment, the first durometer of the first material is between 0 sh OO-70 sh A based on Shore Durometer testing, and the second durometer of the second material is between 40 HRB-70 HRC based on Rockwell Hardness testing.

The retaining component may comprise a plurality of vertically stacked ring structures. In an embodiment of the device, each of two or more of the plurality of vertically stacked ring structures comprises an annular body comprising the first material and a resilient ring comprising the second material, and wherein the annular body overlays the resilient ring and forms an outer periphery of vertically stacked ring structure. In a further embodiment, the thickness of the first material of the annular body between the resilient ring and an outer circumferential periphery of the vertically stacked ring structure is between 1 mm and 20 mm. In another embodiment, the first material and the second material have either or both of different flexural modulus and different durometer.

BRIEF DESCRIPTION OF THE ACCOMPANYING DRAWINGS

DETAILED DESCRIPTION

Figure 1A:
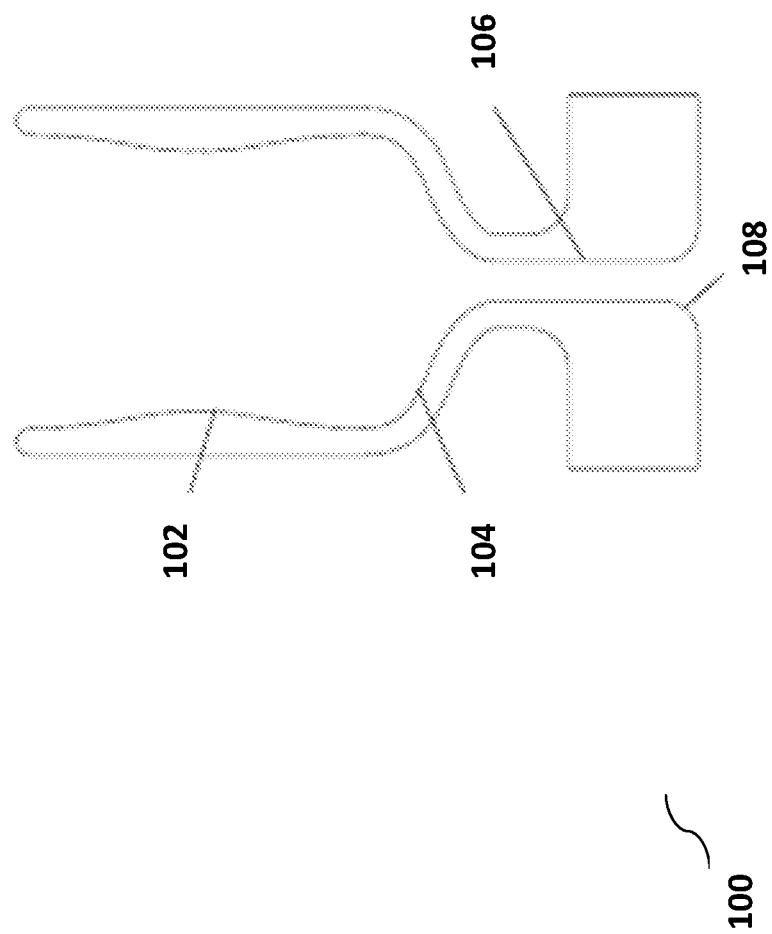
FIGS. 1A and 1B illustrate portions of human rectal anatomy.

The invention comprises a device for collection of fecal discharge and which includes a retaining component for retaining a part of the device within the rectum, coupled with a collection component for collecting stool or liquid discharge received from the rectum. The device may additionally include a fluid delivery component to enable delivery of fluid to the colon, and/or a withdrawal component to support safe removal of the device from the patient.

The invention may also include an insertion component to constrain the retaining component in a collapsed state during placement into the rectum, As described in more detail below, the retaining component may comprise a flexible and resilient substantially "ring-like" structure defining a lumen or passage within the periphery thereof. The retaining component is caused by its resilient properties to naturally expand from a collapsed state having a small cross sectional area to an expanded state having a larger cross sectional area. The resilient properties of the retaining component ensures that in an expanded configuration the retaining component presses against the rectal walls, causing the external peripheral surface(s) of the retaining component to resiliently conform to adjacent rectal walls and to ensure that a complete seal is created between the external periphery of the retaining component and the rectal walls—thereby ensuring that any stool or fecal discharge passes through the lumen of the retaining component instead of leaking through spaces between the external periphery and adjacent rectal walls.

The collection component (or transit sheath) comprises a bag, chute or tube made of a thin, low-friction, flexible, skin friendly material that has an open first end through which stool or fluid may enter said collection component. The first end of the collection component may be coupled with the retaining component such that stool or liquid discharge entering the lumen of the retaining component passes into the collection component through the open proximal end of said collection component. The collection component may be configured to hold and contain material that passes into it through the open proximal end. The other end of the collection component may in an embodiment be a closed end, so as to ensure that the stool or liquid discharge is retained within the collection component.

The insertion component may take any number of different forms. In one, the insertion component is a type of obdurator that is able to be fragmented or disassembled, within which the retaining component is confined in a compressed state. The obdurator may be used to deliver the retaining component into a subject's rectum (in the compressed state), and the retaining component is thereafter released from confinement within the obdurator—thereby permitting it to transition to an expanded state. The obdurator is subsequently withdrawn from the rectum, while the expanded retaining component remains within the subject's rectum. Since the retaining component is coupled to the collection component, stool or fluid discharge from the rectum entering the retaining component transits into the collection component, which is at least partially positioned outside the rectum.

The fluid delivery component comprises an assembly configured to deliver fluid from an external source to the subject's rectum while the retaining component is positioned within the rectum. The fluid delivery component comprises a fluid conduit having an open proximal end, a distal end and a lumen connecting the two—and may in an embodiment comprise a length of tubing or piping of appropriate diameter. The fluid delivery component may be coupled with one or both of the retaining component and the collection component such that when the retaining component is positioned within a subject's rectum, the open proximal end is positioned within the subject's colon while the distal end lies outside of the rectum. The lumen connecting the two ends provides a fluid passageway that enables fluid to be delivered from the distal end through the open proximal end and to the subject's colon. As a result of the configuration, the fluid delivery component enables delivery of enema fluid into the subject's rectum once the retaining component has been positioned within the rectum.

The withdrawal component comprises a structure or assembly that is configured to change either or both of the orientation and/or cross-section of the retaining component to enable withdrawal of the retaining component from the rectum. In an embodiment discussed in this invention the withdrawal component and the fluid delivery component may comprise a single component.

Specific embodiments of the above are discussed in greater detail below.

Figure 1B:
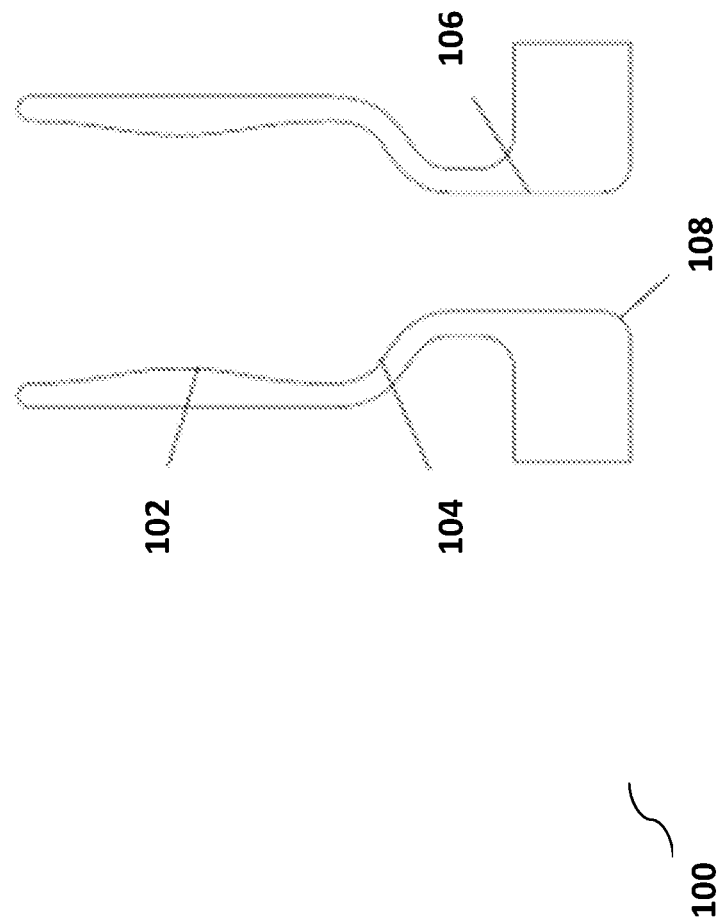

FIG. 1A illustrates the relevant portions of the human rectum 100, including rectal walls 102, the anorectal junction 104, the anal canal 106, and the anal verge 108. In FIG. 1A, anal canal 106 is shown in a constricted position. FIG. 1B depicts the same portions of the rectal anatomy but with the anal canal 106 now in an expanded position (for example when the subject is passing stool).

Figure 2A:
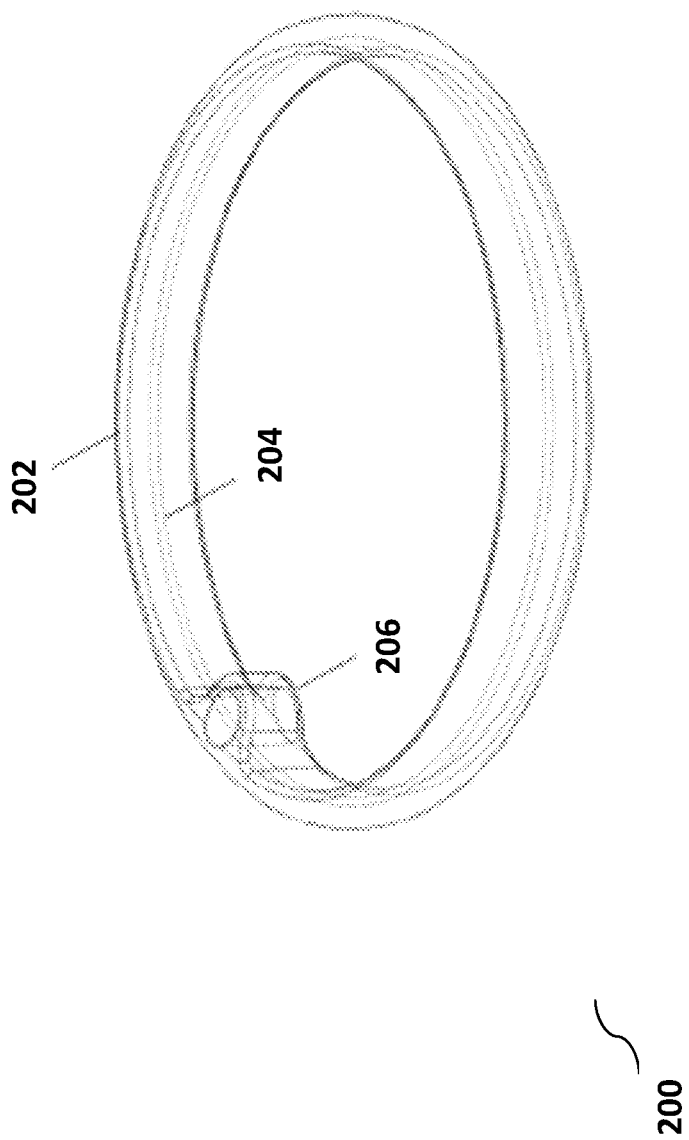
FIG. 2A illustrates an embodiment of a retaining component in an expanded state in accordance with the present invention.

FIG. 2A illustrates an embodiment of the retaining component 200 in an expanded state. Retaining component 200 comprises a pliant and collapsible annular body 202 comprising a first material and a resilient ring 204 comprising a second material, with resilient ring 204 embedded within said annular body 202. Annular body 202 may additionally include a port (or retaining cavity) 206 for housing or holding an end of the fluid delivery component.

Owing to the fact that it is comprised of collapsible annular body 202 and a resilient ring 204 embedded therewithin, retaining component 200 can be collapsed into a number of different configurations to reduce its cross-sectional profile for the purposes of delivering it into a subject's rectum.

Figure 2B:
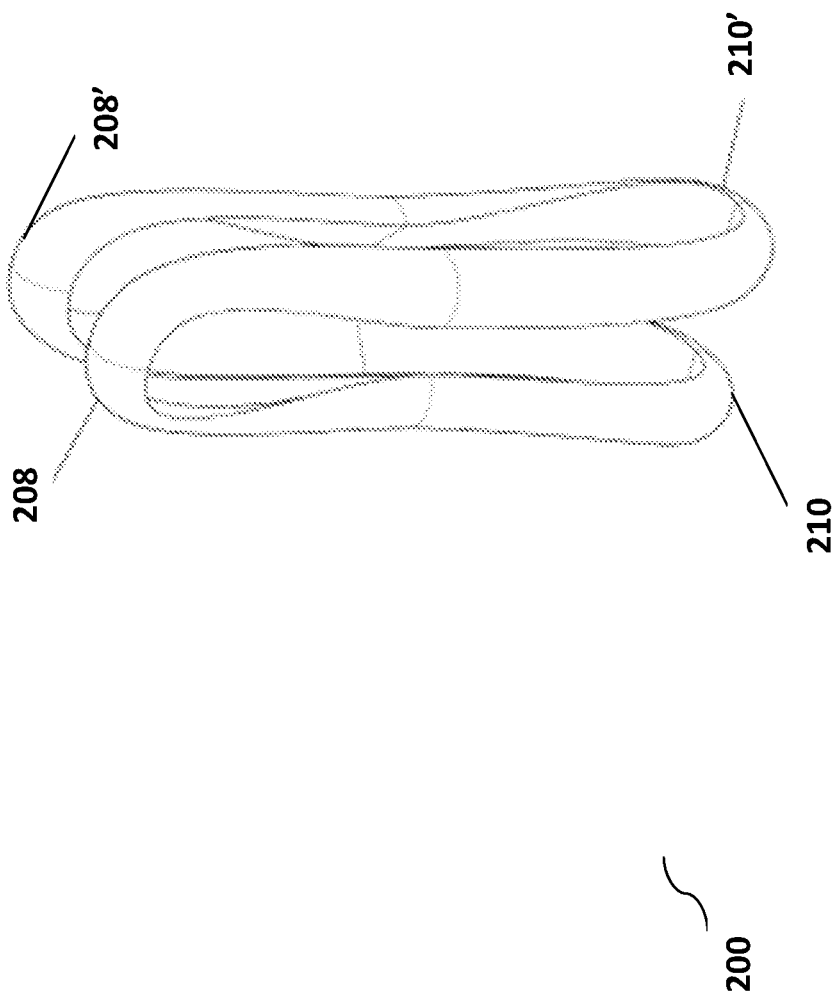
FIGS. 2B and 2C illustrate configurations in which the retaining component may be collapsed.

FIG. 2B illustrates a first exemplary configuration into which retaining component 200 can be collapsed—wherein in said collapsed state, retaining component 200 has been compressed and collapsed along two mutually perpendicular axes to form two peaks 208, 208' and two troughs 210, 210'.

Figure 2C:
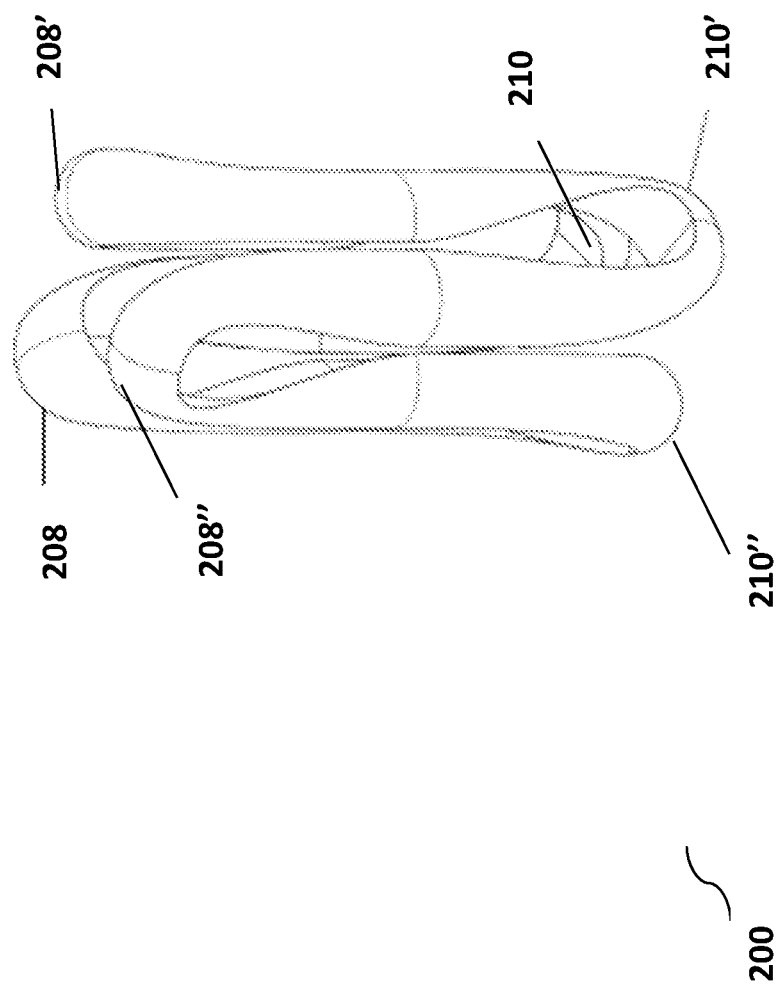

FIG. 2C illustrates a second exemplary configuration into which retaining component 200 can be collapsed—wherein in said collapsed state, retaining component 200 has been compressed and collapsed along three axes, each arranged with 120 degrees between them, to form three peaks 208, 208', 208" and three troughs 210, 210', 210".

It would be understood that the embodiments of FIGS. 2B and 2C are only exemplary and that retaining component 200 can be collapsed into any number of other compressed configurations. However, it will be noted by comparing the embodiments of FIGS. 2B and 2C to the illustrated embodiment in FIG. 2A, that in its collapsed state, the cross-sectional profile of retaining component 200 is substantially reduced—enabling convenient insertion into and withdrawal from a subject's rectum.

Figure 3:
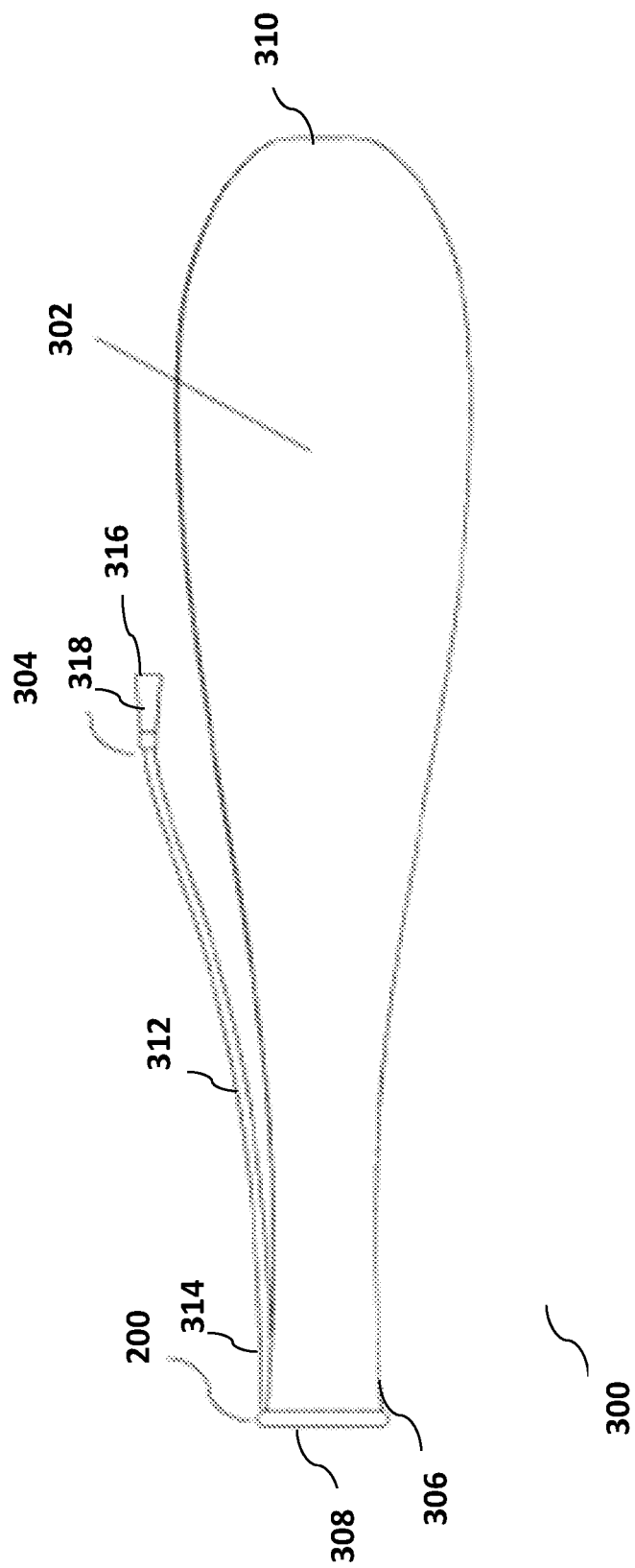
FIG. 3 illustrates an assembled device for collection of fecal discharge in accordance with embodiments of the present invention.

FIG. 3 illustrates an assembled device 300 for collection of fecal discharge, said device 300 comprising retaining component 200 for retaining a part of the device within the rectum, coupled with a collection component 302 for collecting stool or liquid discharge received from the rectum, and a fluid delivery component 304 for delivery of fluid to the colon. In the illustrated embodiment, and as discussed in further detail below, the fluid delivery component 304 may also act as a withdrawal component to support safe removal of the device 300 from a patient's rectum.

As illustrated in FIG. 3, collection component 302 comprises a bag (or alternatively a chute or tube) made of a thin, low-friction, flexible, skin friendly material that has an open first end 306 through which stool or fluid may enter said collection component 302. The open first end of collection component 302 may be coupled with retaining component 200 such that stool or liquid discharge entering an annular opening 308 formed by the retaining component 200, passes into the collection component 302 through first open end 306 of said collection component 302. The collection component 302 may be configured to hold and contain material that passes into it through the open proximal end. In an embodiment, this is achieved by ensuring that a second end 310 of collection component 302 is a closed end.

Also shown in FIG. 3 is fluid delivery component 304—which comprises an assembly configured to deliver fluid from an external source to the subject's rectum while the retaining component 200 is positioned within the rectum. Fluid delivery component 304 comprises a fluid conduit 312 having a first open end 314 positioned proximal to retaining component 200 and a second open end 316 positioned distal to retaining component 200. As shown in FIG. 3, second open end 316 of fluid delivery component 304 may include a connector 318, which enables fluid delivery component 304 to be connected to a fluid source. Fluid from the fluid source may enter second open end 316, pass through fluid conduit 312 and be delivered into a subject's rectum through first open end 314 of fluid conduit 312. Referring back to FIG. 2A, in an embodiment of the invention, fluid conduit 312 or first open end 314 of said fluid conduit 312 may be housed or held within port (or retaining cavity) 206 of retaining component 200—which ensures that when retaining component 200 is disposed within a subject's rectum, first open end 314 of fluid conduit 312 is also disposed within the subject's rectum, thereby enabling fluid to be delivered to the subject's rectum or colon through fluid delivery component 304.

Figure 4:
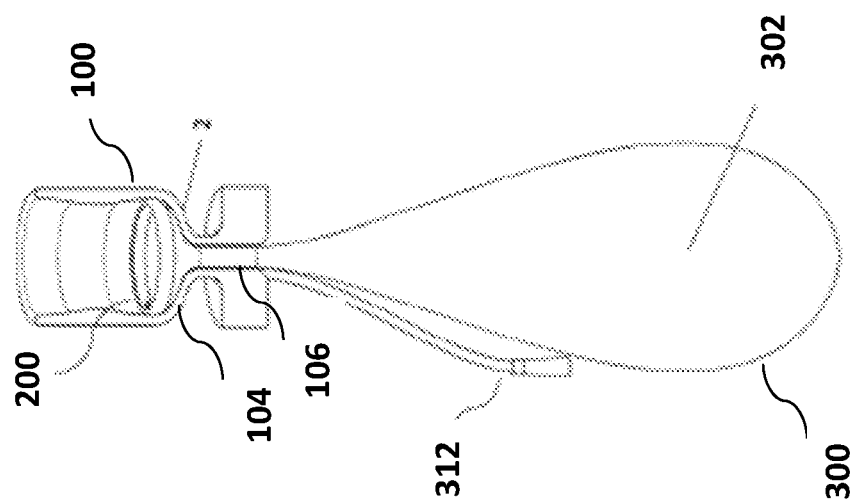
FIG. 4 illustrates an exemplary instance of a device for collection of fecal discharge, positioned within a patient's rectum.

FIG. 4 illustrate an exemplary instance of device 300 for collection of fecal discharge positioned within a patient's rectum 100. As shown in FIG. 4, retaining component 200 is positioned within the subject's rectum 100 above the shelf structure formed by the subject's anorectal junction 104. Owing to the distance between the walls of the rectum 100 above the anorectal junction 104, retaining component 200 has transitioned to its expanded state, and in its expanded state rests securely on the walls of the anorectal junction 104. Since the distance between the walls of the anal canal 106 beneath the anorectal junction are narrower than the expanded cross section of retaining component 200 in its expanded state, retaining component 200 is securely held by anorectal junction 104 and accidental withdrawal of retaining component 200 from the subject's rectum is prevented.

It would be understood that retaining component 200 may be delivered to a position above the anorectal junction 104 by compressing retaining component 200 into a configuration having a cross-section less than the cross-section of anal canal 106, delivering said retaining component 200 (while remaining in a compressed configuration) through anal canal 106 to a position above anorectal junction 104, and thereafter releasing retaining component 200 from the applied compressive forces—thereby allowing retaining component 200 to transition to its expanded state, in which expanded state, it naturally resists withdrawal through the narrower anal canal 106.

As shown in FIG. 4, first ends of collection component 302 and fluid delivery component 304 (each of which have an end affixed to or in proximity to retaining component 200), respectively trail said retaining component 200 into the rectum, while opposite ends of said collection component 302 and fluid delivery component 304 pass through anal canal 106 and are located outside of rectum 100.

As in the case of insertion, removal of retaining component 200 (and consequently of device 300) from a subject's rectum requires application of forces that cause retaining component to transition from an expanded state to a compressed state having an orientation or cross-section sufficient to enable retaining component 200 to be withdrawn through anal canal 106 by application of withdrawing force. In an embodiment, retaining component 200 may be caused to change orientation or collapse into a sufficiently compressed state to enable withdrawal through anal canal 106 by application of (i) withdrawing force (in a direction distal to the rectum) at a plurality of points distributed around a periphery of retaining component 200 (which withdrawing force may be applied by one or more tethers provided on the periphery of retaining component 200)—which causes retaining component 200 to collapse or transition to a collapsed state, whereinafter continued application of withdrawing force in a direction distal to the rectum causes retaining component 200 (and device 300 as a whole) to be withdrawn from the subject's rectum.

An embodiment of the invention is particularly configured to resolve certain serious shortcomings in other prior art devices that rely on annular retaining components to serve as indwelling components within a subject's rectum. Before discussing the specific invention embodiment, reference to FIGS. 5A to 5D provides information on the specific shortcoming that is sought to be resolved.

Figure 5B:
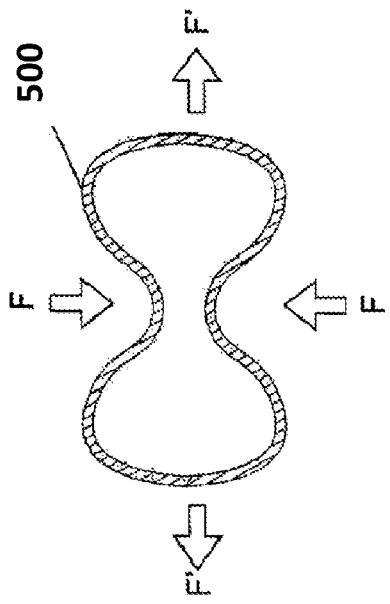
FIGS. 5A and 5B illustrate exemplary responses of prior art retaining components to inwardly directed forces of the type typically observed within the rectal anatomy.
Figure 5D:
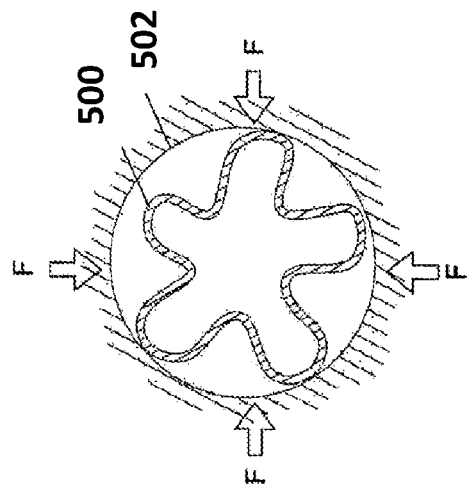
FIGS. 5C and 5D illustrate exemplary responses of retaining components constructed according to the teachings of the present invention, to inwardly directed forces of the type typically observed within the rectal anatomy.
Figure 5A:
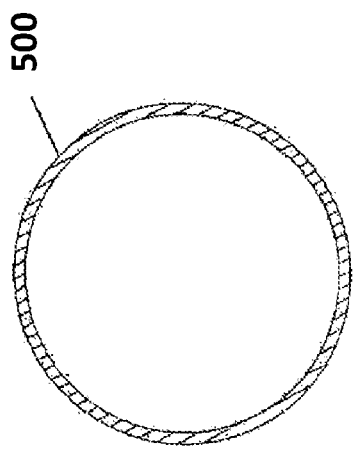

FIG. 5A illustrates a retaining component 500 of the kind observed in prior art devices is in its fully expanded state, and assumes a uniformly circular (or substantially circular) shape. FIG. 5B demonstrates the effect of inwardly directed forces F along certain points on the circumference of said retaining component 500, in that portions of the resilient member on which inward forces F are directed, deform inwards, while other portions are correspondingly deformed outwards. Since retaining component 500 in such prior art devices is a resilient ring, the respective inward and outward deformation is a consequence of the resilient properties of the constituting material.

Figure 5C:
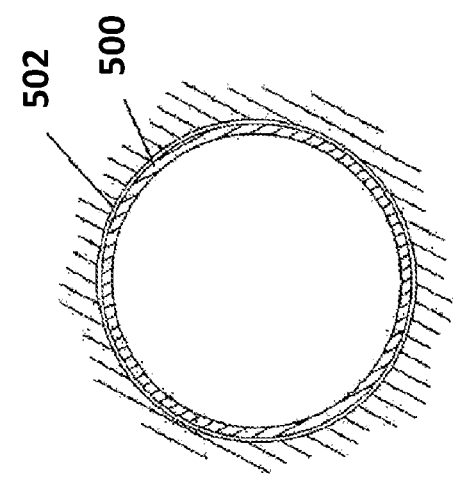

FIG. 5C illustrates retaining component 500 in its fully expanded state when disposed within a subject's rectum. Adjacent rectal walls 502 are illustrated in a relaxed state, wherein no inwardly directed forces are applied on retaining component 500. In FIG. 5D, the rectal walls 502 are illustrated undergoing a peristaltic contraction, wherein inwardly directed radial forces F are applied at various points on the circumference of retaining component 500. Since the inwardly directed compressive forces F are applied across the circumference of retaining component 500, said member 500 is forced to collapse inwardly into one or more inward deformations, with a view to reduce the circumferential surface area presented by retaining component 500 adjacent to rectal walls 502. The inward deformations create gaps between rectal wall 502 and circumference of retaining component 500, through which fecal matter or fluid within the rectum can pass, leading to seepage or leakage along the outside of the device.

The invention addresses this problem through the specific constructional parameters of retaining component 200.

As described above, retaining component 200 comprises a pliant and collapsible annular body 202 comprising a first material and a resilient ring 204 comprising a second material and embedded within or affixed to said annular body 202. The first material used for the pliant and collapsible annular body 202 is different from and has different properties from the second material used for resilient ring 204 embedded within or affixed to annular body 202. In an embodiment of the invention, resilient ring 204 is affixed to annular body 202 such that the outer periphery of retaining component 200 is entirely comprised of annular body 202— i.e. said annular body 202 buffers the rectal anatomy from contact with resilient ring 204 at all points along the outer periphery of retaining component 200.

In an embodiment of the invention, the first and second materials are selected to have different flexural modulus values—wherein the first material has a significantly lower flexural modulus than the second material. More specifically, the first material forming the pliant and collapsible annular body 202 has a flexural modulus of between 100 KPa and 100 MPa, while the second material forming the resilient ring 204 has a flexural modulus of between 20 GPa and 210 GPa.

In a more preferred embodiment, the first and second materials are additionally selected to have different durometers—wherein the first material has a significantly lower hardness than the second material. More specifically, the first material forming the pliant and collapsible annular body 202 has a durometer (or hardness) value of between 0 sh OO-70 sh A (based on Shore Durometer testing), and the second material forming the resilient ring 204 has a durometer (or hardness value) of between 40 HRB-70 HRC (based on Rockwell Hardness testing).

In an embodiment of the invention, the second material is any of one or more shape memory or superelastic alloys; various forms of spring metal such as steel, titanium, or beryllium copper; thermoplastic or thermoset polymers.

In an embodiment of the invention, the first material is any of absorbent materials; open cell or closed cell foams; and/or other natural or synthetic materials having elastic, resilient, and/or compliant properties.

In a yet more preferred embodiment of the invention, the retaining component 200 is configured such that the outward radial pressure exerted by resilient ring 204 is between 5 mmHg to 100 mmHg. Yet further, retaining component 200 may be configured so that the thickness of the first material between resilient ring 204 and an outer circumferential periphery of retaining component 200 is between 1 mm to 20 mm.

It has been found that by configuring retaining component 200 in accordance with the constructional embodiments discussed hereinabove and particularly owing to the selected differential properties of the first and second materials discussed above, even in cases where inwardly directed radial forces (for example peristaltic forces) are applied to retaining component 200 by adjacent walls of the rectal anatomy, and even in cases where non-uniform contact surfaces (for example overlap with rectal folds or residual stool) are not avoidable, collapsible annular body 202 is caused to compress and form inward indentations together with moving anatomy and non-uniform surfaces while ensuring to not separate from the adjacent rectal walls, while resilient ring 204 does not significantly change shape or orientation, acting as the main structure—thereby ensuring that patency of the fluid seal formed between the outer periphery of retaining component 200 and walls of the rectum is maintained—and preventing or minimizing leakage or seepage of fecal discharge or fluid that is contained within the rectum, outside of the device 300 for collection of fecal discharge.

Figure 6:
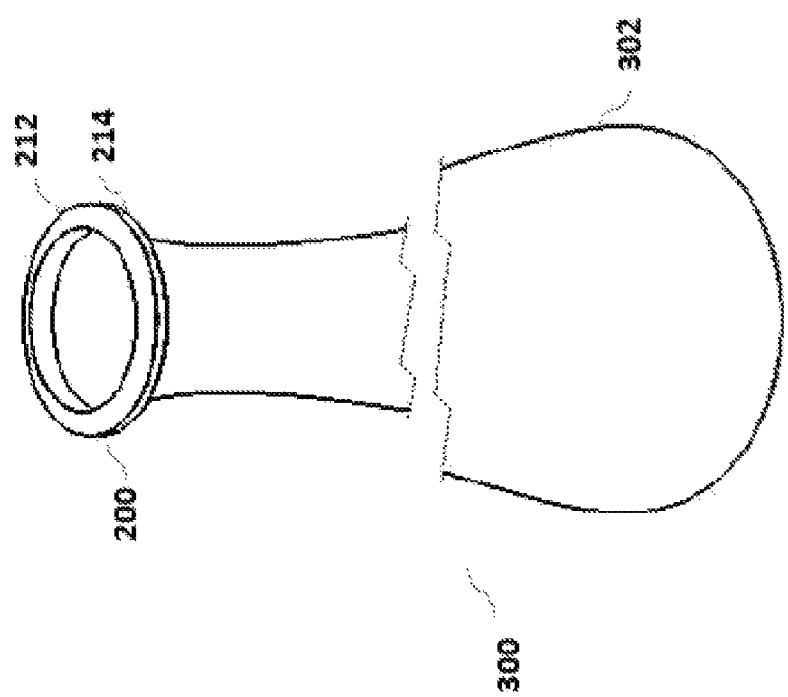
FIG. 6 illustrates a specific embodiment of a device for collection of fecal discharge constructed in accordance with the teachings of the present invention.

FIG. 6 illustrates a preferred embodiment of the device 300 for collection of fecal discharge, comprising retaining component 200 and collection component 302. In the illustrated embodiment, retaining component 200 comprises a plurality of vertically stacked ring structures 212, 214. Each of said plurality of vertically stacked ring structures 212, 214 may comprise comprises a pliant and collapsible annular body comprising a first material and a resilient ring comprising a second material and embedded within or affixed to said annular body. It would be further understood that one or more than one or all of the vertically stacked ring structures 212, 214 may be configured in accordance with any of the preferred features of construction that have described above in this specification, including based on the above described parameters for flexural modulus, durometer, thickness and radial pressure. By implementing a retaining component 200 having a plurality of vertically stacked ring structures 212, 214, the FIG. 6 embodiment ensures that even if particulate fecal matter or fluid within a subject's rectum leaks or seeps past the outer periphery of a first ring structure 212, it would be prevented from continuing to leak or seep outside of the device 300 by the next ring structure 214.

While FIG. 6 illustrates an embodiment comprising two vertically stacked ring structures 212, 214, it would be understood that any number of such ring structures may be arranged in a vertical stack.

While the exemplary embodiments of the present invention are described and illustrated herein, it will be appreciated that they are merely illustrative. It will be understood by those skilled in the art that various modifications in form and detail may be made therein without departing from or offending the spirit and scope of the invention as defined by the appended claims. Additionally, the invention illustratively disclose herein suitably may be practiced in the absence of any element which is not specifically disclosed herein—and in a particular embodiment that is specifically contemplated, the invention is intended to be practiced in the absence of any one or more elements which are not specifically disclosed herein.

What is claimed is:

1. A device for collection of fecal discharge, comprising:
    a retaining component configured for deployment within a subject's rectum and having an annular cross-section, said annular cross-section of the retaining component forming a fluid inlet into an open end of a collection component affixed to said retaining component and forming a receptacle for matter discharged from a subject's rectum, wherein:
        said retaining component comprising an annular body comprising a first material and a resilient ring comprising a second material, wherein the annular body overlays the resilient ring and forms an outer circumferential periphery of the retaining component, and wherein:
            the resilient ring is configured to exert outward radial pressure of between 5 mmHg and 100 mmHg;
            the thickness of the first material of the annular body between the resilient ring and the outer circumferential periphery of the retaining component is between 1 mm and 20 mm;
            the first material and the second material have different flexural modulus, wherein the first flexural modulus of the first material is between 100 KPa and 100 MPa and the second flexural modulus of the second material is between 20 GPa and 210 GPa; and
        the retaining component is collapsible in response to compression into at least one of:
            a first collapsed state, wherein the retaining component is collapsed along two mutually perpendicular axes to form two peaks and two troughs; and
            a second collapsed state, wherein the retaining component is collapsed along three axes, each arranged with 120 degrees between them, to form three peaks and three troughs.

2. The device as claimed in claim 1, wherein a first durometer of the first material is lower than a second durometer of the second material.

3. The device as claimed in claim 2, wherein the first durometer of the first material is between 0 sh OO—70 sh A based on Shore Durometer testing, and the second durometer of the second material is between 40 HRB—70 HRC based on Rockwell Hardness testing.

4. The device as claimed in claim 1, wherein the retaining component comprises a plurality of vertically stacked ring structures forming a vertically stacked ring structure.

5. The device as claimed in claim 4, wherein each of the plurality of vertically stacked ring structures comprises:
    an annular body comprising the first material and a resilient ring comprising the second material, and wherein the annular body overlays the resilient ring and forms an outer periphery of the vertically stacked ring structure, and wherein:
        the thickness of the first material of the annular body between the resilient ring and an outer circumferential periphery of the vertically stacked ring structure is between 1 mm and 20 mm; and
        the first material and the second material have different durometers.

6. The device as claimed in claim 1, wherein the resilient ring is embedded within the annular body.

7. The device as claimed in claim 1, wherein the retaining component is collapsible in response to compression into either of the first collapsed state and the second collapsed state.

* * * * *